US006482390B1

(12) United States Patent
Hiscocks et al.

(10) Patent No.: US 6,482,390 B1
(45) Date of Patent: Nov. 19, 2002

(54) AEROSOL FORMULATIONS AND METHOD

(75) Inventors: Peter Gerard Hiscocks, Hartson (GB); David Laurence Gee, Harston (GB)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/467,486

(22) Filed: Dec. 20, 1999

Related U.S. Application Data

(62) Division of application No. 08/930,600, filed as application No. PCT/EP96/01561 on Apr. 21, 1996, now Pat. No. 6,023,836.

(30) Foreign Application Priority Data

Apr. 13, 1995 (GB) ............................................. 9507768

(51) Int. Cl.[7] ............................ A61L 9/04; A61K 9/14
(52) U.S. Cl. ........................................ 424/45; 46/489
(58) Field of Search ............................ 424/45, 46, 489

(56) References Cited

U.S. PATENT DOCUMENTS

| | | | |
|---|---|---|---|
| 3,190,508 A | | 6/1965 | Peterson |
| 3,996,153 A | | 12/1976 | Heeb et al. |
| 4,139,607 A | | 2/1979 | Simons et al. |
| 4,335,121 A | | 6/1982 | Phillipps et al. |
| 4,655,959 A | * | 4/1987 | Stopper |
| 5,169,433 A | | 12/1992 | Lindsay et al. |
| 5,190,029 A | * | 3/1993 | Byron et al. |
| 5,225,183 A | * | 7/1993 | Purewal et al. |
| 5,225,445 A | | 7/1993 | Skidmore et al. |
| 5,301,664 A | | 4/1994 | Sievers et al. |
| 5,674,472 A | * | 10/1997 | Akehurst et al. |
| 5,891,420 A | * | 4/1999 | Cutie |

FOREIGN PATENT DOCUMENTS

| | | |
|---|---|---|
| EP | 101036 | 2/1984 |
| EP | 037277 | 6/1990 |
| EP | 616953 | 9/1994 |
| EP | 067733 | 10/1995 |
| EP | 0675054 | 10/1995 |
| EP | 0671218 | 10/1997 |
| FR | 2615124 | 11/1988 |
| WO | 9104011 | 4/1991 |
| WO | 9111173 | 8/1991 |
| WO | 9111495 | 8/1991 |
| WO | 9114422 | 10/1991 |
| WO | 9317665 | 9/1993 |
| WO | 9503984 | 2/1995 |
| WO | 9503985 | 2/1995 |
| WO | 9714407 | 4/1997 |

OTHER PUBLICATIONS

R. Bodmeier et al., Pharmaceutical Research, vol. 12, No. 8 (1995).

* cited by examiner

Primary Examiner—Jose G. Dees
Assistant Examiner—Robert M DeWitty
(74) Attorney, Agent, or Firm—Christopher P. Rogers

(57) ABSTRACT

A hand held apparatus and method for creating an aerosolized mist of particles is described. The apparatus comprises a high pressure vessel containing a solution or suspension of the substance to be aerosolized in a high pressure liquefied gas, a manually actuatable valve and a spray nozzle. The high pressure liquefied gas is in a sub-critical state.

32 Claims, 4 Drawing Sheets

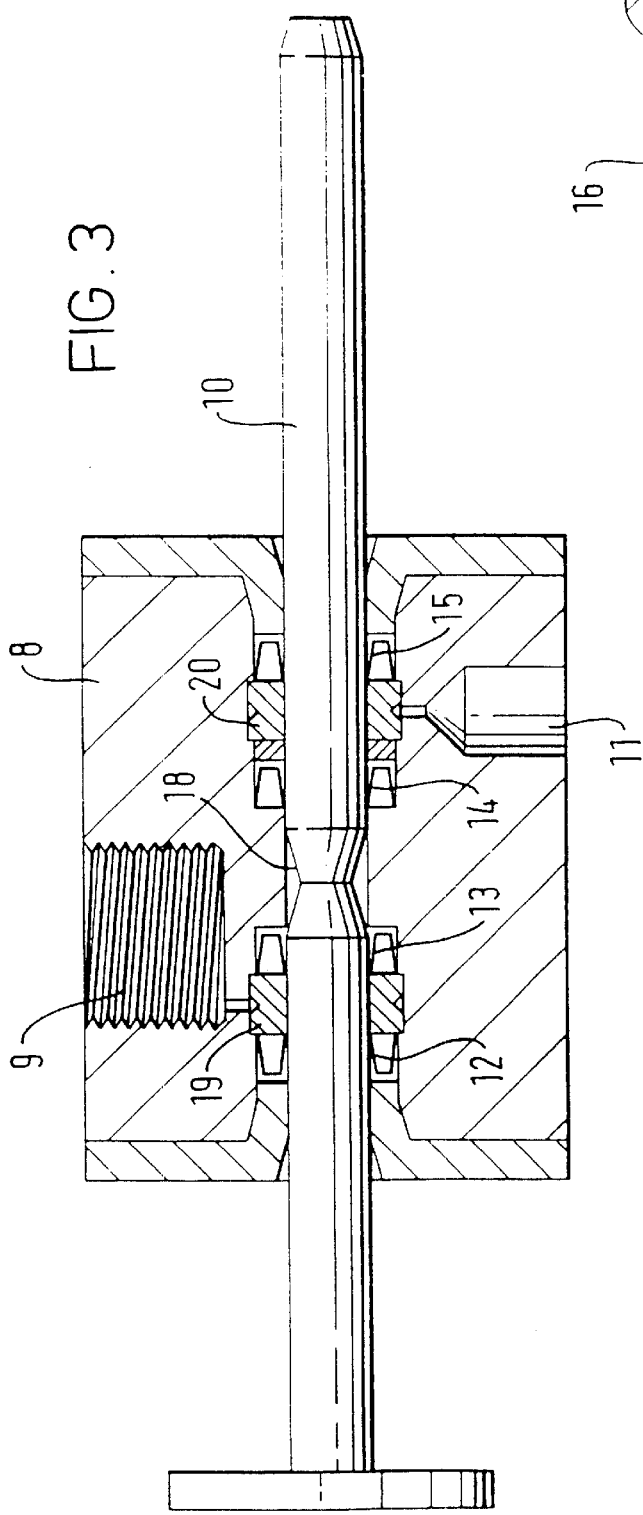
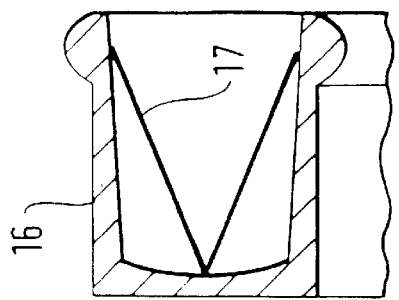

AEROSOL FORMULATIONS AND METHOD

This application is a divisional of co-pending application No. Ser. 08/930,600, filed on Oct. 29, 1997, now U.S. Pat. No. 6,032,836, issued Mar. 3, 2000. Application Ser. No. 08/930,600 is the national phase of PCT International Application No. PCT/EP96/01561 filed on Apr. 21, 1996 under 35 U.S.C. §371. The entire contents of each of the above-identified applications are hereby incorporated.

This invention relates to a method and apparatus for dispensing a material in aerosol form. It is particularly, though not exclusively, concerned with metered dose medicament aerosols, for example metered dose inhalers (MDIs).

BACKGROUND OF THE INVENTION

Aerosol type dispensers are used throughout the world for dispensing a wide range of products, for example hair lacquer, furniture polish, cleaners, paint, insect killers and medicaments.

Liquefied compressed gases are invariably used as the propellant for aerosol dispensers for inhalation therapy in preference to non-liquefied compressed gasses such as nitrogen or carbon dioxide, as they confer the following critical advantages:

a) the spray undergoes flash evaporation to give aerosols of very small particle size b) the spray particle size remains constant during pack emptying as the inhaler vapour pressure is maintained at an almost constant level by progressive propellant evaporation c) the pressure generated by partial evaporation of propellant in the valve metering chamber causes efficient discharging of the metered valve contents and accurate dose delivery d) suitably designed formulations have notably good chemical drug stability and resistance to microbial growth.

Figure 1B:
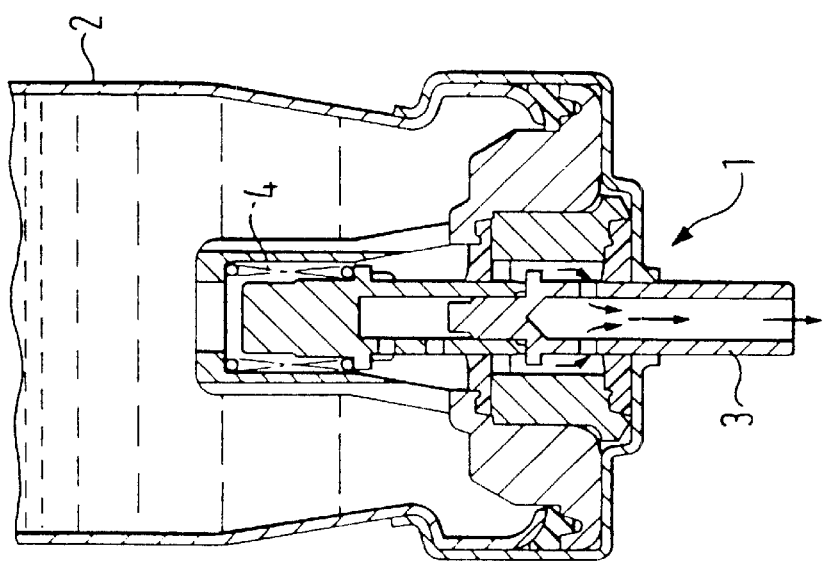
Figure 1A:
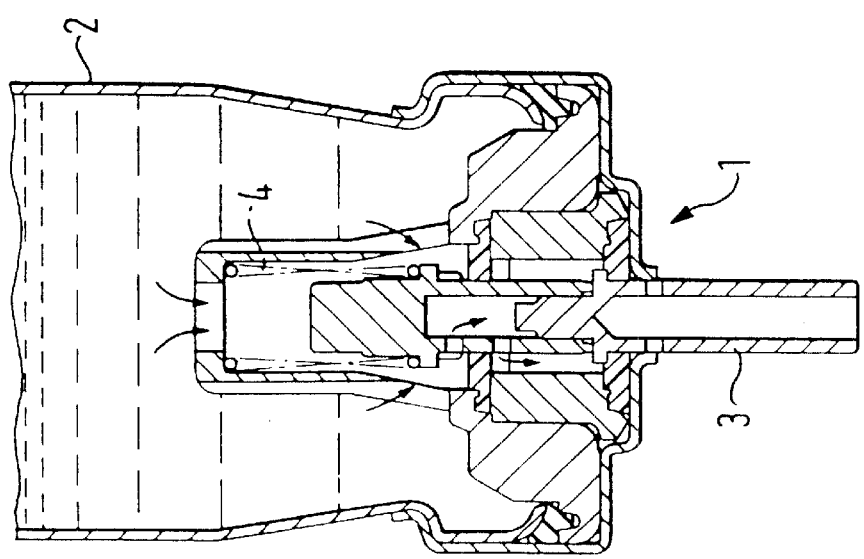
Figure 5A:
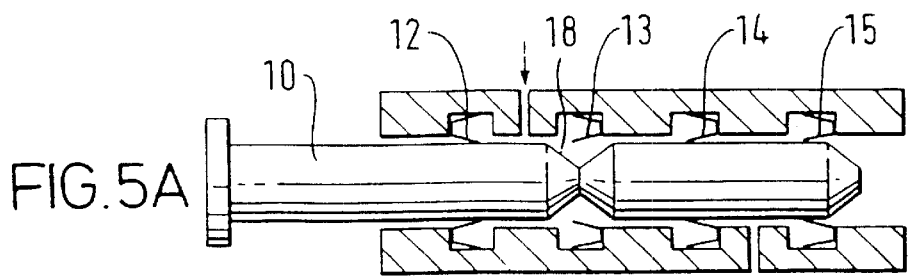
Figure 5B:
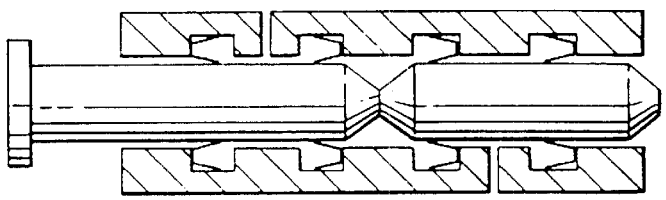
Figure 5C:
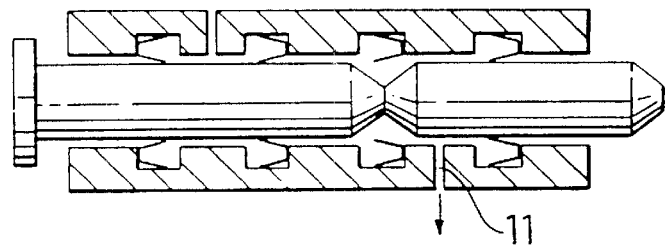

FIGS. 1A and 1B of the accompanying drawings show the valve and lower portion of a typical MDI aerosol dispenser in closed and open positions respectively. Such dispensers generally comprise a small aluminium shuttle valve 1 which is crimp fitted to the can 2 containing the drug and chlorofluorocarbon (CFC) propellants. The valve is activated by manually pressing shuttle pin 3 such that it moves a small distance into the can 2. In order to do this it is necessary to overcome the force exerted on the pin 3 by virtue spring 4 and of the pressure within the container. Pressures within such dispensers are typically around 8 bar which is sufficient to maintain CFC propellants in a liquid state at ambient temperatures.

Until recently, CFCs were the most common of the propellant gases used in aerosols because they are inert, miscible with a wide range of products, are easily liquefied under low pressures, give a substantially constant product flow-rate, and can produce sprays of droplets having mean diameters in the range of 3 to over 100 micrometers. However, in the 1970's it was proposed that CFCs were probably responsible for depleting the Earth's protective ozone layer, and in 1987, most countries signed the Montreal Protocol to phase out the use of CFCs and have since agreed to stop use of CFCs for non-essential applications by the end of 1995. One notable exemption to this deadline for cessation of use is in relation to MDIs for medicaments, which are regarded as an essential use of CFCs, but even this use of CFCs will be phased out as acceptable alternatives are developed.

Many companies are now working to develop alternative CFC—free propellants for use in aerosol spray devices including MDIs to overcome the ozone destructing properties of conventional CFC containing propellants. A class of propellants which are believed to have minimal ozone-depleting effects in comparison to conventional CFCs comprise fluorocarbons and hydrogen-containing fluorocarbons (commonly known as HFA propellants), and a number of medicinal aerosol formulations using such propellant systems are disclosed in, for example European Patent Application Publication No. 0372777 and PCT Patent Application Nos. WO91/04011, WO91111173, WO91/11495 and WO91114422. These applications are all concerned with the preparation of pressurised aerosols for the administration of medicaments and seek to overcome the problems associated with the use of the new class of propellants, in particular the problems of stability associated with the pharmaceutical formulations prepared. The applications all propose the addition of one or more of adjuvents such as alcohols, alkanes, dimethyl, ether, surfactants and even conventional chlorofluorocarbon propellants in small amounts to minimise potential ozone damage. Surfactants are added to make the suspension formulations stable. However, whilst surfactants may conveniently be used in MDIs which use CFC propellants, surfactants are not generally solvent in HFA propellants and so require the use of additional co-solvents.

Attempts have also been made to develop devices which produce satisfactory spray characteristics making use of compressed gases such as nitrogen and carbon dioxide, which are present in the atmosphere in relatively large proportions. The main problem associated with aerosol dispensers of this type which use compressed gas propellant is that whilst the spray characteristics may be satisfactory when the dispenser is full and the propellant is at a high pressure, they display a serious drop in pressure during emptying as the available headspace increases with the result that the atomizing and spray pattern deteriorate to an extent that dispensing becomes unsatisfactory for many purposes. Such dispensers may be used where such deterioration of the atomization and spray pattern are of no concern, e.g. in the dispensing of foodstuffs, but it has not been found to be useful in areas where atomization and spray patterns are important, e.g. in dispensing of medicaments. For this latter application it is often required to deliver drugs to topically treat the lung or to provide a route for absorption into the blood stream of drugs that are poorly absorbed from the alimentary tract. To reach the alveoli it is essential that the aerodynamic size of the particles is less than 10 micrometers, preferably between 0.5 and 5 micrometers. In order to reliably reproduce aerosol sprays from a dispenser in which the majority of particles have a size of between 0.5 and 5 micrometers it is necessary to maintain a fairly constant propellant pressure.

The pressures that would be required to maintain gases such as carbon dioxide in a liquid state at ambient temperatures are typically of the order of 10 times greater than that within a conventional dispenser such as that shown in FIGS. 1A and 1B, and such pressures are far in excess of those within any dispensers currently available. Hence to maintain the same activation force, the shuttle pin diameter would need to be reduced accordingly resulting in more stringent engineering requirements.

U.S. Pat. No. 5,301,664 describes an apparatus for producing a gasborne dispersion of a physiologically active solute dissolved in a supercritical fluid solvent. The supercritical fluid solution is passed into a subcritical region to evaporate the solvent and form an aerosol cloud of the solute particles. Some of the problems associated with this device are that: (i) the temperature and pressure of the reservoir must be maintained above the critical temperature and pressure of the solvent in order to maintain supercritical conditions, and (ii) to ensure consistent delivery of solute dose upon each actuation of the valve it is necessary to either reduce the reservoir volume each time a dose is delivered by the magnitude of the volume dispensed to maintain solute density, or increase the dose size accordingly.

European Patent Application 675054 (published after the priority date of this application) describes a constant quantity injection valve and canister for carbon dioxide however it does not discuss the use of solutions or suspensions of substances in carbon dioxide, nor does it mention use of the valve in an apparatus for inhalation therapy. Furthermore, since opening of the valve requires the pressure inside the canister to be overcome, the arrangement is disadvantageous when the carbon dioxide is under very high pressure.

European Patent Application 677332 (published after the priority date of this application) describes a method and apparatus for producing fine particles of substance which comprises dissolving the substance in a first liquid, mixing the resultant solution with a second fluid (such as supercritical carbon dioxide) and then rapidly lowering the pressure. However this method may not be suitable for all substances and the apparatus is relatively complex since it requires control of a mixing step. Furthermore, if the solvent of the first liquid is itself soluble in the second fluid, the dissolved substance may start to recrystallise in an uncontrolled manner prior to the pressure being lowered.

SUMMARY OF THE INVENTION

European Patent Application 671218 describes a method of generating an aerosol using a liquefied gas propellant. Medical agents are described which are dissolved or suspended in a liquefied gas to be aerosolized, wherein the medical agents have a particle size of 0.5 μm or below when suspended in the liquefied gas to be aerosolized.

It is an object of the present invention to provide a method and apparatus for generating aerosol mists which overcomes the aforementioned disadvantages or which is of more general application or which achieves the desired end with greater ease or simplicity.

According to the present invention there is provided a hand held apparatus for creating an aerosolised mist of particles, the apparatus comprising a high pressure vessel containing a solution or suspension of the substance to be aerosolised in a high pressure liquefied gas which is in a subcritical state, a manually actuatable valve and a spray nozzle.

DETAILED DESCRIPTION OF THE INVENTION

We particularly envisage that the valve will be a metering valve. Thus, the valve may comprise a body having an inlet in communication with the high pressure vessel, an outlet in communication with the spray nozzle, and a metering member including a metering chamber mounted in the body which is adapted to move between a first position in which it is in communication with the inlet and a second position in which it is in communication with the outlet.

In a preferred embodiment of the invention, the metering member is defined by a shaft and the metering chamber is a cut-away section of the shaft. Thus the valve body is provided with a bore, the metering member is defined by a shaft, the metering chamber is a cut-away section of the shaft and the shaft is seated in the bore.

Preferably both ends of the bore will be open to the atmosphere.

In a particularly preferred embodiment of the invention the valve comprises a body with an inlet and an outlet, a shaft with a cut away section mounted in the body and moveable between a first position in which the cut away section is in communication with the inlet, and a second position in which the cut away section is in communication with the outlet, and wherein the shaft and inlet are arranged such that the force required to actuate the valve by movement of the shaft between the first and second positions is substantially independent of the pressure at the inlet.

Such an embodiment has the advantage that the user of the apparatus will not have any difficulty in causing actuation of the valve even when the pressure inside the high pressure vessel is very high. More particularly the pressure that can be tolerated inside the high pressure vessel is limited by the strength of that vessel and the operating parameters of the apparatus (for example the requirement to keep the gas in a sub-critical state) and not by the strength of the user. Furthermore, the manufacture of apparatus parts is not expected to cause any particular engineering difficulty.

In one convenient arrangement which has the advantage of symmetry and ease of manufacture, the shaft and inlet are arranged such that the valve is actuated by movement of the shaft between the first and second positions along an axis which is orthogonal to the axis along which the pressure at the inlet is exerted. In the above arrangements, seals will be disposed between the body and the shaft to prevent the escape of liquefied gas. Ideally, seals will be arranged such that the inlet is at all times isolated from the outlet irrespective of the position of the shaft. For example there may be disposed 2 pairs of seals such that when the metering chamber is in the first position a first pair of seals keeps the metering chamber in communication with the inlet and isolated from the outlet and when the metering chamber is in the second position a second pair of seals keeps the metering chamber in communication with the outlet and isolated from the inlet.

Although a number of alternatives can be envisaged, we find it useful to use polytetrafluoroethylene (PTFE) lip seals with an integral spring. PTFE is a particularly suitable sealing material because it does not absorb carbon dioxide, does not require lubrication, does not contain carcinogenic compounds and is food grade. PTFE is non-elastomeric and so requires an integral spring to maintain a seal. Alternative seal designs or materials, e.g. ultra-high molecular weight polyethylene, could also be used.

An alternative embodiment of the invention which does not have the advantage that the force required to actuate the valve by movement of the shaft between the first and second positions is substantially independent of the pressure at the inlet, but which does nonetheless have the advantage that the burden on the user to actuate the valve may be significantly eased is set out in the following embodiment.

In this embodiment, we provide an apparatus wherein the valve inlet is provided with a pin valve comprising a pin biased against a seat and the shaft includes a ramped surface such that in the first position the pin of the pin valve is displaced from its seat to allow communication between the high pressure vessel and the metering chamber and in the second position the pin of the pin valve is seated to prevent communication between the high pressure vessel and the metering chamber and wherein the displacement of the pin from its seat against the bias is caused by urging of the ramped surface against the pin upon movement of the shaft between the first and second positions.

The arrangement is especially convenient when the valve body is provided with a second outlet and when the shaft includes a second ramped surface which cooperates with the first ramped surface such that the shaft may move between the first position in which the metering chamber is in communication with the inlet and the second position in which the metering chamber is in communication with one of the two outlets on moving the shaft laterally in either direction within the bore.

The apparatus will also desirably be provided with seals which are arranged such that the inlet is at all times isolated from the outlet or outlets irrespective of the position of the shaft.

As a further improvement, the high pressure vessel may be provided with an integral valve assembly comprising a member biased against a seat such that when the high pressure vessel is engaged with the metering valve inlet the vessel valve member lies in close proximity to the pin of the metering valve pin valve such that on actuation of the metering valve the pin of the metering valve pin valve is pushed off its seat and abuts against the vessel valve member which is in turn pushed off its seat thereby bringing the inlet into communication with the interior of the vessel. The advantage of this arrangement is that the valve of the apparatus may readily be engaged and disengaged from the high pressure vessel thus facilitating replacement or renewal of the contents of the vessel.

Figure 6:
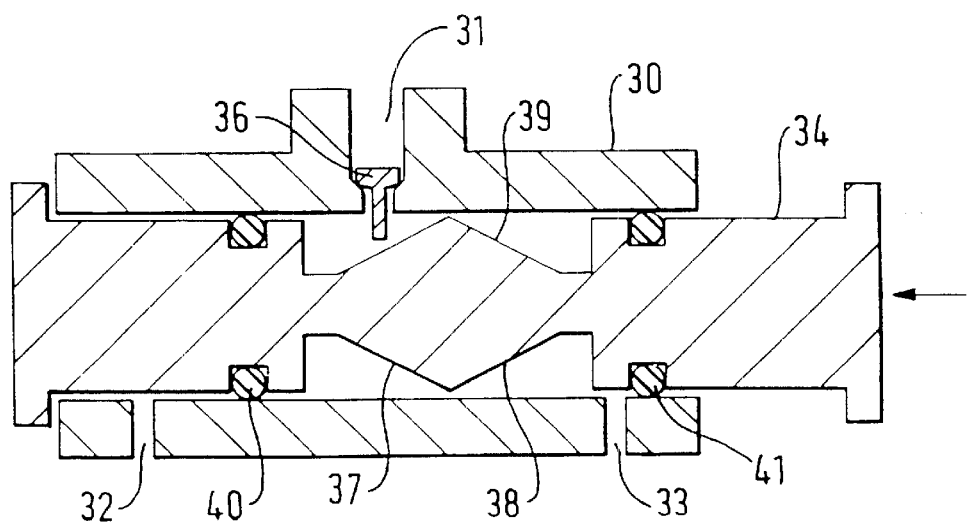
Figure 7:
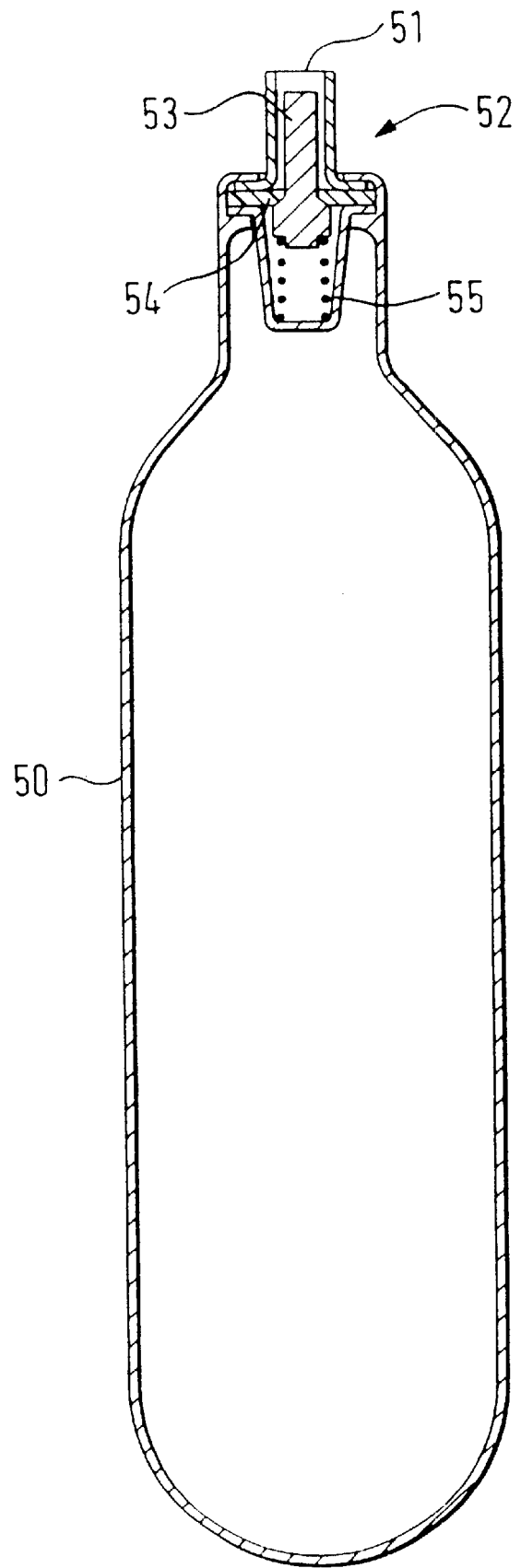

According to another aspect of the invention there is also provided a method for creating an aerosolised mist of particles which comprises forming a solution or suspension of the substance to be aerosolised in a high pressure liquefied gas which is in a sub-critical state and rapidly expanding the solution or suspension at the spray nozzle of an apparatus according to the invention.

As a consequence of using a high pressure liquefied gas, the propellant will flash off from the droplets more rapidly than conventional propellants thereby decreasing the likelihood that drug laden droplets will impact on the throat of the patient and, as a consequence, increase the efficiency with which drug is delivered to the lungs.

High-pressure liquefied gases will typically be those that liquefy at ambient temperature at a pressure of greater than 25 bar. More usually they will liquefy at a pressure in excess of 55 bar and may be up to 150 bar.

As the temperature of a liquid increases, its density decreases whilst as the pressure of a gas increases, its density increases. At the critical point, the density of both phases becomes the same so that the two phases are indistinguishable. By “in a subcritical state” we mean that the high pressure liquefied gas will not be become “supercritical” i.e. be above both its critical temperature and pressure (as determined from the phase diagram of the gas) under all useful operating conditions of the apparatus. For example the pressure of the liquefied gas will not be so great that the gas becomes supercritical at a temperature below say 30° C.

Whilst the critical temperature and pressure are documented for particular gases, for example:

| Gas | Critical Pressure (bar) | Critical Temperature (° C.) |
|---|---|---|
| Carbon dioxide | 74 | 31 |
| Nitrous oxide | 72 | 36 |
| Sulphur hexafluoride | 37 | 45 |

-continued

| Gas | Critical Pressure (bar) | Critical Temperature (° C.) |
|---|---|---|
| Ethane | 48 | 32 |
| Trifluoromethane | 47 | 26 | these values will tend to be modified by the presence of other components in a formulation containing the liquefied gas.

Gases considered to be especially suitable for carrying out the method of the current invention include carbon dioxide, nitrous oxide and sulphur hexafluoride. Carbon dioxide and nitrous oxide are the preferred gases, especially carbon dioxide. Mixture of such gases may also be used. Such gases do not deplete atmospheric ozone, act as good solvent or suspension media, provide good propellant characteristics for droplet or particle cloud generation, and reduce the need for excipients, especially co-solvents.

Carbon dioxide in liquefied form behaves as a particularly good solvent so that surface active agents to stabilise suspensions may be dissolved therein without the need for additional co-solvents. Furthermore, upon expansion into the atmosphere it undergoes substantially instantaneous flash evaporation giving rise to an aerosol mist of the active ingredient with very small particle sizes.

Substances suitable for delivery in this way include pharmaceuticals especially pharmaceuticals destined for inhalation such as salbutamol, beclomethasone dipropionate, salmeterol and fluticasone propionate and pharmaceutically acceptable salts thereof. Other pharmaceuticals destined for inhalation include cromoglycate, nedocromil, ipratropium, terbutaline, formoterol, budesonide and reproterol and pharmaceutically acceptable salts thereof.

Depending on the properties of the active ingredient and its solubility or otherwise in the liquefied gas propellant, excipients might be used to improve the formulation characteristics.

In order to improve the properties of a suspension formulation it may be desired to dissolve or disperse a surfactant in the liquefied gas. A co-solvent may likewise be included in the liquefied gas in order to improve the properties of solution or suspension formulations. As to whether a suspension or solution of the substance to be dispensed may be preferred and the concentrations thereof as well as the use and concentrations of excipients such as co-solvents, surfactants or diluents will depend on the solubility and other properties of the substance to be dispensed in the propellant.

Preferred embodiments of the invention are described below, by example only, with reference to the accompanying drawings, wherein:

BRIEF DESCRIPTION OF THE DRAWINGS

FIGS. 1A and 1B are partial cross-sectional views of the hand-held apparatus shown in FIG. 2. In FIG. 1A, the valve is in the closed position. In FIG. 1B, the valve is in the open position.

FIG. 2 shows a plain view of a hand held-apparatus according to the invention;

FIG. 3 shows a section through a metering valve according to one embodiment of the invention;

FIG. 4 shows a section through a seal used in the metering valve of FIG. 3;

FIGS. 5A–5C show sections through the metering valve of FIG. 3 at different stages during operation of the valve;

FIG. 6 shows a section through a metering valve according to a second embodiment of the invention; and FIG. 7 shows a section through a reservoir with an integral valve assembly suitable for use with the metering valve of FIG. 6.

Figure 2:
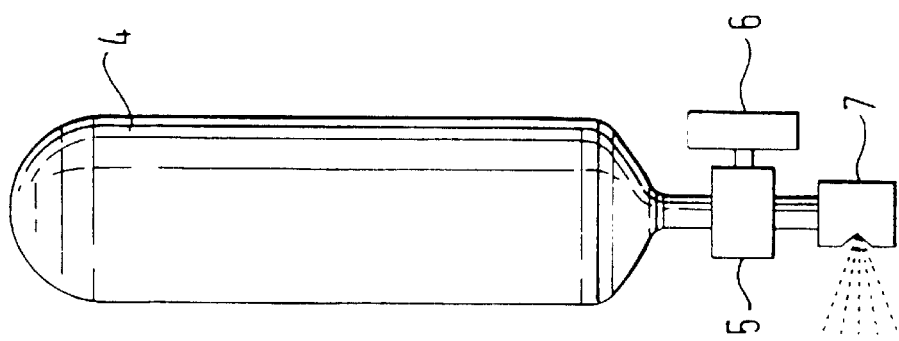

The apparatus according to the invention shown in FIG. 2 comprises a hand held high pressure vessel or reservoir 4 containing a suspension of salbutamol sulphate suspended in liquefied carbon dioxide connected to a metering valve 5 with actuating button 6 capable of handling high pressure liquefied gas and being manually actuatable, and a spray nozzle 7. The suspension has a concentration of 32 mg salbutamol sulphate in 8 mg carbon dioxide, and is maintained at a pressure of around 60 bar.

The high pressure vessel 4 is of the type commonly available as a source of high pressure carbon dioxide for soda syphons. The vessel is of metallic construction but might also be formed of any other suitable high strength material. The vessel may be provided with a rupturable closure member as is common on soda syphon-type vessels, or alternatively may be provided with a valve arrangement to control flow from the vessel. A vessel provided with a valve arrangement is shown in FIG. 7 and is described in more detail below.

The metering valve mechanism is shown in FIG. 3 and includes a body 8 with a screw thread for mounting the high pressure vessel at inlet 9. The body 8 might be provided with a piercing element (not shown) for piercing a rupturable closure on the high pressure vessel or a valve actuating mechanism to open the valve arrangement on the high pressure vessel. The body 8 is formed with a bore therethrough for receiving a shaft 10, and an outlet 11 leading to a spray nozzle (not shown). Four seals 12, 13, 14, 15 are provided within the bore.

FIG. 4 shows a section through one of the seals which comprises a PTFE lip seal 16 with an integral metal spring 17.

The shaft 10 is formed with a cut away section in the form of a chamfered groove 18 which in co-operation with the bore delineates the metering chamber. The metering chamber is sized to contain a 50 micro-litre dose. However, the size of the metering chamber may be varied according to the delivery characteristics required.

Two channelled circlips 19, 20 are arranged within the bore to maintain the spacing between seals pairs 12, 13 and 14, 15, whilst the channels ensure communication between chamfered groove 18 and the inlet 9 and outlet 11 respectively depending upon the position of shaft 10.

The shaft 10 and inlet 9 are arranged such that the forces exerted on the shaft by virtue of the pressure in the vessel are in equilibrium since the effective area presented by the shaft and upon which the pressure acts is the same for both directions of movement of the shaft. The force required to move the shaft is therefore substantially independent of the pressure within the vessel.

FIGS. 5A, 5B and 5C illustrate the operation of the valve mechanism. FIG. 5A shows the valve in the ‘primed’ position in which the high pressure fluid from the reservoir is contained between seals 12 and 14. To meter a quantity of fluid the shaft 10 is moved into the position depicted in FIG. 5B. The metered volume is that contained between seals 13 and 14 and can be varied by altering the dimensions of the chamfered groove 18.

The metered volume of fluid may be dispensed out of the outlet 11 by moving the shaft 10 into the position depicted in FIG. 5C. As the chamfered groove 18 passes seal 14 a path is established to outlet 11 for the metered volume of fluid. The high pressure required to maintain the metered volume of fluid in liquefied form is thus vented to the atmosphere via outlet 11. As a result the liquefied carbon dioxide propellant undergoes substantially instantaneous flash evaporation as it expands through the outlet 11. As the propellant flows through outlet 11 it carries with it the volume of active ingredient suspended therein, and the flash evaporation gives rise to an aerosol mist of 200 micro-grams salbutamol sulphate with particles of a respirable size. In the position shown in FIG. 5C the reservoir pressure is contained by seals 12 and 13. Seal 15 ensures that no fluid escapes out of the end of the valve mechanism. After delivery of the metered volume of fluid the shaft is moved back into the position depicted in FIG. 5A under the action of a spring (not shown) and the valve is re-pimed and ready for actuation again.

One advantage of using a metering valve of the type described is that the force required for operation is substantially independent of reservoir pressure. The valve can therefore be actuated comfortably by application of finger pressure on the end of shaft 10.

An alternative metering valve is illustrated in FIG. 6. The metering valve comprises a body 30 with a suitable means for mounting the reservoir (not shown) at inlet 31. The body 30 is also provided with two outlets 32, 33 for connection to a spray nozzle (not shown), and a bore for receiving shaft 34. A pin valve 36 is located at inlet 31. Shaft 34 is formed with two cut away sections of reduced diameter separated by two symmetrical conical sections creating ramped surfaces 37, 38. The sections of reduced diameter and ramped surfaces 37, 38 form a single chamber 39 within the bore. Seals 40, 41 are provided between bore and shaft 34 to prevent escape of fluid from chamber 39 through the ends of the valve mechanism.

To actuate the valve from the position shown in FIG. 6 the user pushes the shaft 34 in the direction of the arrow. As the shaft 34 moves within the bore, seal 41 35 moves across outlet 33 to seal chamber 39 therefrom, and pin valve 36 is pushed off its seat by the ramped surface 37 so allowing the liquefied solution or suspension to enter chamber 39 from the reservoir through inlet 31. As the shaft approaches the end of its travel ramped surface 38 allows pin valve 36 to close, and as seal 40 moves across outlet 32 the metered volume of fluid contained within chamber 39 is dispensed out of outlet 32.

Due to its symmetrical configuration subsequent actuation of the valve is achieved by pushing the shaft 34 in the reverse direction to that indicated by the arrow in FIG. 6. The metering and dispensing process is now exactly the same as that described above, except that the roles of outlets 32, 33, ramped surfaces 37, 38 and seals 40, 41 respectively are reversed.

The metering valve illustrated in FIG. 6 might conveniently be mounted to a reservoir with an integral valve assembly which enables safe removal of the reservoir from the metering valve without allowing escape of the contents of the reservoir. An example of such a reservoir is depicted in FIG. 7. The reservoir comprises a high pressure vessel 50 with an outlet 51, and a valve arrangement 52 which in a closed position prevents flow of the reservoir contents out of the outlet 51, and in an open position allows flow out of the outlet 51.

The valve arrangement 52 includes a valve member 53 which, in the closed position, seats against valve seat 54 to prevent flow through the valve, and in the open position is pushed off the valve seat 54 in a proximal direction with respect to the vessel 50 to allow flow past the valve member 53 and valve seat 54 to outlet 51. The valve member 53 is biassed to its closed position by means of spring 55 andlor the pressure within the reservoir such that, unless acted on by an external force, the valve will remain in the closed position.

When connected to the metering valve of FIG. 6, outlet 51 is mounted at metering valve inlet 31 such that valve member 53 lies in close proximity to pin valve 36. Upon actuation of the metering valve, pin valve 36 is pushed off its seat and abuts against valve member 53 which in turn is also pushed off its seat, so allowing the contents of the reservoir to enter chamber 39. At the end of the actuation stroke of the metering valve, valve arrangement 52 closes as pin valve 36 and valve member 53 return to their respective seats. At any time the reservoir may be removed from the metering valve without allowing escape of its contents to enable, for example, replacement of the reservoir. Alternatively, valve member 53 and pin valve 36 might be replaced by a single pin which forms part of valve arrangement 52 and which protrudes beyond outlet 51 such that upon actuation of the metering valve it is pushed off its seat by direct contact with ramped surfaces 37 and 38.

What is claimed is:

1. An aerosol formulation, comprising:
    sub-critical, high-pressure, liquefied gas, wherein said sub-critical, high-pressure, liquefied gas is selected from the group consisting of carbon dioxide, nitrous oxide, sulphur hexafluoride, and mixtures thereof;
    a pharmaceutical in suspension in said liquefied gas, wherein the pharmaceutical is selected from the group consisting of salbutamol, beclomethasone dipropionate, salmeterol, fluticasone propionate, cromoglycate, nedocromil, ipratropium, terbutaline, formoterol, budesonide, reproterol and pharmaceutically acceptable salts thereof; and wherein the pharmaceutical has an aerodynamic size of 0.5–10 µm; and
    optionally one or more additional excipients.

2. The aerosol formulation of claim 1, wherein the excipients are selected from the group consisting of surfactants, co-solvents and diluents.

3. The aerosol formulation of claim 1, wherein said gas is carbon dioxide.

4. The aerosol formulation of claim 1, wherein said gas is nitrous oxide.

5. The aerosol formulation of claim 1, wherein said pharmaceutical suitable for inhalation.

6. The aerosol formulation of claim 1, wherein said pharmaceutical is fluticasone propionate.

7. The aerosol formulation of claim 1, wherein the pharmaceutical is suspended in said liquefied gas.

8. The aerosol formulation of claim 1, wherein the pharmaceutical has a particle size of between 0.5 and 5 micrometers in said suspension.

9. An aerosol formulation, comprising:
    sub-critical, high-pressure, liquefied gas, wherein said sub-critical, high-pressure, liquefied gas is selected from the group consisting of carbon dioxide, nitrous oxide, sulphur hexafluoride, and mixtures thereof;
    a pharmaceutical in solution or in suspension in said liquefied gas, wherein the pharmaceutical is selected from the group consisting of salbutamol, beclomethasone dipropionate, salmeterol, fluticasone propionate, cromoglycate, nedocromil, ipratropium, terbutaline, formoterol, budesonide, reproterol and pharmaceutically acceptable salts thereof; and
    optionally one or more additional excipients.

10. The aerosol formulation of claim 9, wherein the excipients are selected from the group consisting of surfactants, co-solvents and diluents.

11. The aerosol formulation of claim 9, wherein said gas is carbon dioxide.

12. The aerosol formulation of claim 9, wherein said gas is nitrous oxide.

13. The aerosol formulation of claim 9, wherein said pharmaceutical is fluticasone propionate.

14. The aerosol formulation of claim 9, wherein the pharmaceutical is suspended in said liquefied gas, and wherein the pharmaceutical has an aerodynamic size of less than 10 micrometers.

15. An aerosol formulation, comprising:
    sub-critical, high-pressure, liquefied carbon dioxide;
    a pharmaceutical in suspension in said liquefied gas, wherein the pharmaceutical is selected from the group consisting of salbutamol, beclomethasone dipropionate, salmeterol, fluticasone propionate, cromoglycate, nedocromil, ipratropium, terbutaline, formoterol, budesonide, reproterol and pharmaceutically acceptable salts thereof;
    and wherein the pharmaceutical has an aerodynamic size of 0.5–10 µm; and
    optionally one or more additional excipients, with the proviso that the formulation does not comprise a co-solvent.

16. The aerosol formulation of claim 15, wherein the pharmaceutical is fluticasone propionate.

17. The aerosol formulation of claim 15, wherein the pharmaceutical is suspended in said liquefied gas.

18. The aerosol formulation of claim 15, wherein the pharmaceutical has an aerodynamic size of between 0.5 and 5 micrometers.

19. An aerosol formulation, comprising:
    sub-critical, high-pressure, liquefied carbon dioxide;
    a pharmaceutical in solution or in suspension in said liquefied gas, wherein the pharmaceutical is selected from the group consisting of salbutamol, beclomethasone dipropionate, salmeterol, fluticasone propionate, cromoglycate, nedocromil, ipratropium, terbutaline, formoterol, budesonide, reproterol and pharmaceutically acceptable salts thereof; and wherein the pharmaceutical has an aerodynamic size of 0.5–10 µm;
    a surfactant; and
    optionally a co-solvent.

20. The aerosol formulation of claim 19, wherein the pharmaceutical is suspended in said liquefied gas.

21. The aerosol formulation of claim 19, wherein the pharmaceutical has an aerodynamic size of between 0.5 and 5 micrometers.

22. A method for creating an aerosolized mist of particles which comprises rapidly expanding the formulation of claim 1 at a spray nozzle of a hand held apparatus containing said formulation.

23. A method for creating an aerosolized mist of particles which comprises rapidly expanding the formulation of claim 9 at a spray nozzle of a hand held apparatus containing said formulation.

24. A method for creating an aerosolized mist of particles which comprises rapidly expanding the formulation of claim 15 at a spray nozzle of a hand held apparatus containing said formulation.

25. A method for creating an aerosolized mist of particles which comprises rapidly expanding the formulation of claim 19 at a spray nozzle of a hand held apparatus containing said formulation.

26. An aerosol formulation, comprising:

sub-critical, high-pressure, liquefied gas, wherein said sub-critical, high-pressure, liquefied gas is selected from the group consisting of carbon dioxide, nitrous oxide, sulphur hexafluoride, and mixtures thereof;

a pharmaceutical in solution or in suspension in said liquefied gas, wherein the pharmaceutical is selected from the group consisting of salbutamol, beclomethasone dipropionate, salmeterol, fluticasone propionate, cromoglycate, nedocromil, ipratropium, terbutaline, formoterol, budesonide, reproterol and pharmaceutically acceptable salts thereof; and optionally one or more additional excipients.

27. The aerosol formulation of claim 26, wherein the excipients are selected from the group consisting of surfactants, co-solvents and diluents.

28. The aerosol formulation of claim 26, wherein said gas is carbon dioxide.

29. The aerosol formulation of claim 26, wherein said gas is nitrous oxide.

30. The aerosol formulation of claim 26, wherein said pharmaceutical is fluticasone propionate.

31. The aerosol formulation of claim 26, wherein the pharmaceutical is suspended in said liquefied gas, and wherein the pharmaceutical has an aerodynamic size of less than 10 $\mu$m in said suspension.

32. An aerosol formulation, comprising:

sub-critical, high-pressure, liquefied gas, wherein said sub-critical, high-pressure, liquefied gas is not above both its critical temperature and its critical pressure;

a pharmaceutical in suspension in said liquefied gas, wherein the pharmaceutical has an aerodynamic size of 0.5–10 $\mu$m in said suspension; and optionally one or more additional excipients.

* * * * *